Jan. 29, 1974 R. YOSHIMURA Plant Pat. 3,462
AZALEA PLANT
Filed March 27, 1972
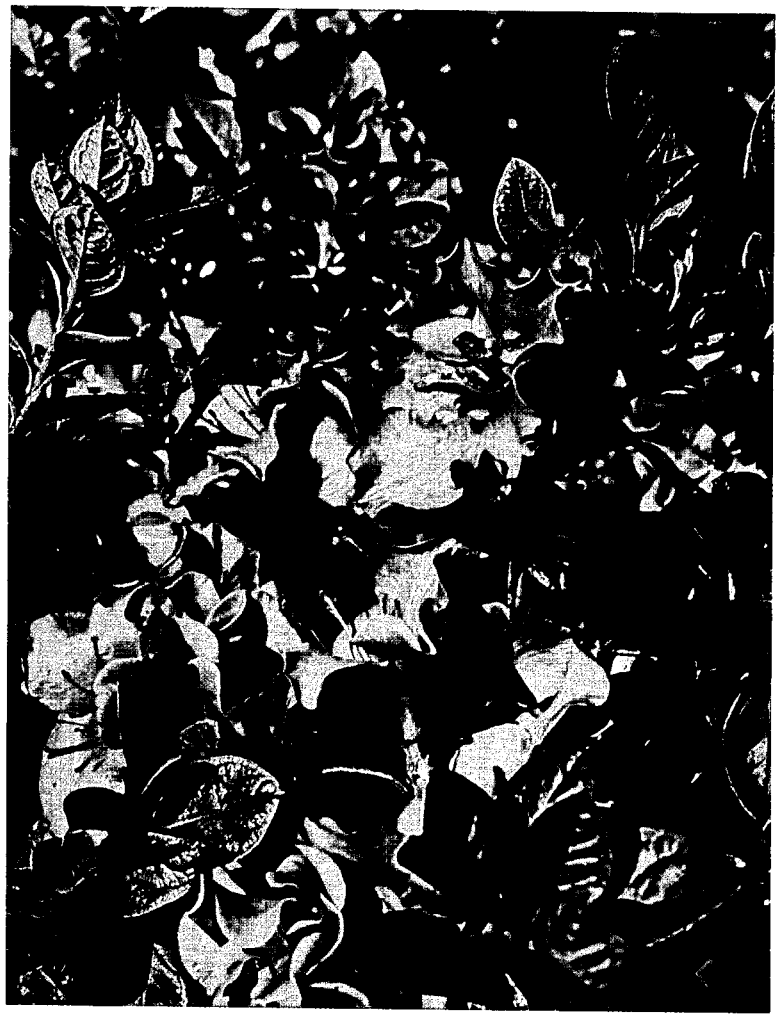
INVENTOR.
RAYMOND YOSHIMURA
BY J. F. Cuneo
ATTORNEY

United States Patent Office

Plant Pat. 3,462

Patented Jan. 29, 1974

3,462
AZALEA PLANT

Raymond Yoshimura, San Gabriel, Calif., assignor to San Gabriel Nursery and Florist, San Gabriel, Calif.

Filed Mar. 27, 1972, Ser. No. 238,702

Int. Cl. A01h 5/00

U.S. Cl. Plt.—57 1 Claim

This invention relates to a new and distinct variety of azalea plant.

The new and distinct variety was discovered by me as a sport growing from a patented variety of azalea plant known as Mission Bells, Plant Pat. No. 2,872, which is cardinal red in color with the central portion of the petals tending to shade to an Indian lake coloration that is present in the form of thin lines. The parent plant was situated in my growing grounds located at San Gabriel, Calif., and also produces flowers that are slightly double.

This sport was discovered by me in the month of February of the year 1968, and differs from its parent plant in that the flowers are predominantly Orient Red whereas those of the parent plant are Cardinal Red shading to a series of centrally located lines that are Indian lake. The new variety has been reproduced asexually at 632 South San Gabriel Blvd., San Gabriel, Calif., from cuttings. All the descendants of this plant have exhibited the distinguishing coloration and other characteristics of this new and distinct variety, and have thereby established that the strain is true; numerous cuttings have been made since the new variety was discovered. The new variety cannot be reproduced true from seed.

The new variety can be grown either as a prodiminantly upright bush or it can be trained to grow as a tree type of plant. The acompanying illustrations, in full color show typical specimens of the flowers and leaves. The colors appearing in the illustrations are as nearly correct as it is possible to reproduce them by this type of illustration. The orangy red color of the flowers was particularly difficult to match. To facilitate the identification of the important colors referred to in the specification, the nomenclature adopted by the British Horticultural Color Charts has been followed. A detailed description of the plant and flowers of this new and distinct species of azalea follows:

THE FLOWER

Locality where grown and observed: San Gabriel, Calif.

Flowers borne: A number of flowers are borne on a stem.

Continuity: The plant will bloom at various times throughout the year but the peak blooming period commences in February in the coastal region of Southern California and continues until the weather becomes quite warm. The flowers will last on the plant from six to eight weeks during cooler weather but have a much shorter duration during the hot summer months.

Bud:

*Before calyx breaks.*—Size: About three-eights to one-half inch in diameter and from one-half to three-quarters of an inch in length.

*As calyx breaks.*—Color: Light green. Sepals: Shape: Substantially elliptic. Size: Range from one-half to three-quarters of an inch in length.

*As first petal opens.*—Size: One and one-half to one and three-quarters of an inch in length, with the width being slightly less. Color: The color is predominantly Orient Red 819/1. Shape: The petals appear to be substantially round and are undulate. Petals are arranged compactly around the base but become more open near and at the tip.

Bloom:

*Size.*—The blooms are from two and one-half to three inches at the widest part.

*Petalage.*—Petals vary from five to nine in number.

*Form.*—Bloom is campanulate, becoming very wide at the outer end.

*Petals.*—Shape: The petals are substantially orbicular at the outer end and become slightly pointed or more obtuse at the base. Margin is usually undulate and some of the petals have one or more notches in the margin. Color: The color varies between Orient Red 819/1 and Orient Red 819.

*General color effect.*—The general overall color effect is an orangy red that is between Orient Red 819/1 and Orient Red 819 when the flowers are in their prime. As the flowers start to wither the color will darken substantially.

*Flower longevity.*—The flowers last up to as long as six to eight weeks during cooler weather but have a much shorter life during warmer weather.

THE PLANT

Foliage:

Leaves.—Leaves are broadly elliptic with the tip apiculate and the base attenuate. Margin of the leaf is slightly ciliate. The surface of the leaves is slightly puberulent. The arrangement of the leaves is alternate.

*Petiole.*—Petiole is usually about five-eighths of an inch in length.

*Veins.*—Veins are pinnate in arrangement and are more prominent on the underside of the leaf than on the upper side. The back of the petiole and main veins is strigose.

*Size of leaves.*—The leaves are from one to one and one-quarter inches in width and from two to two and one-quarter inches in length when fully matured.

*Color of leaves.*—Upper Side of Leaf: Parsley Green 00962. Under Side of Leaf: Willow Green 000862.

Growth habit: Plant is classed as a moderate grower. The plant can grow from twelve to fifteen inches in one year and if permitted, the plant will grow to a height of six feet. This new variety can be grown either as a predominantly upright bush or it can be trained to form a tree type of plant.

Main stems: When trained as a bush the main stems can reach one inch in diameter. When trained as a tree the trunk will usually reach a diameter of one and one-quarter inches or slightly larger diameter.

REPRODUCTIVE ORGANS

Stamens: Stamens vary from none to eight.

Filaments: Filaments are the same in number as the stamens.

Anthers: Anthers vary from none to eight in number.

Pollen:

*Quantity.*—Average quantity.

*Color.*—Whitish in color.

Ovaries: Ovaries are not visible being covered with fine white hair.

Having described my invention, I claim:

1. The new and distinct variety of azalea plant substantially as herein shown and described, characterized particularly as to novelty by the slightly double, campanulate, substantially Orient red blooms borne in profusion during the winter and spring months, there being many blooms on a stem, by its flowering habit that extends throughout a substantial portion of the year, and by its vigorous upright growth habit.

No references cited.

ROBERT E. BAGWILL, Primary Examiner